(12) United States Patent
Israel

(10) Patent No.: US 6,966,913 B2
(45) Date of Patent: Nov. 22, 2005

(54) INTRAOCULAR RING

(76) Inventor: Henry M. Israel, 39 Ben Zakai Street, Bnei Brak 51482 (IL)

(*) Notice: Subject to any disclaimer, the term of this patent is extended or adjusted under 35 U.S.C. 154(b) by 427 days.

(21) Appl. No.: 10/152,005

(22) Filed: May 22, 2002

(65) Prior Publication Data

US 2003/0220652 A1     Nov. 27, 2003

(51) Int. Cl.[7] ............................................. A61F 9/00

(52) U.S. Cl. ....................... 606/107; 623/6.38

(58) Field of Search ................ 606/107; 623/6.22, 623/6.37–6.38, 6.12

(56) References Cited

U.S. PATENT DOCUMENTS

| | | | | |
|---|---|---|---|---|
| 4,878,910 A | * | 11/1989 | Koziol et al. | 623/6.38 |
| 5,628,795 A | * | 5/1997 | Langerman | 623/4.1 |
| 6,063,118 A | * | 5/2000 | Nagamoto | 623/6.12 |
| 2002/0138141 A1 | * | 9/2002 | Zadno-Azizi et al. | 623/6.43 |

* cited by examiner

Primary Examiner—(Jackie) Tan-Uyen T. Ho
(74) Attorney, Agent, or Firm—Dekel Patent Ltd.; David Klein

(57) ABSTRACT

Apparatus including an intraocular ring comprising a circumferential wall, the ring being adapted to receive therein an intraocular lens (IOL) implant, and the wall being formed with at least one aperture for passing therethrough a haptic of the IOL implant. A dialing member may extend from a portion of the ring, adapted for grasping and turning the ring about a central axis thereof.

10 Claims, 5 Drawing Sheets

US 6,966,913 B2

INTRAOCULAR RING

FIELD OF THE INVENTION

The present invention relates generally to intraocular devices useful in ophthalmologic procedures, such as cataract surgery, and particularly to an intraocular ring which may be useful for mounting therein intraocular lens implants, and for reducing or preventing posterior capsule opacification (PCO).

BACKGROUND OF THE INVENTION

As is well known, in cataract surgery, an opaque natural lens is replaced by an artificial intraocular lens (IOL). A known postoperative complication of such surgery, associated with decreased vision, is posterior capsule opacification (PCO), generally caused by epithelium cells growing between the lens capsule and the IOL. PCO is commonly treated by YAG or Nd:YAG laser capsulotomy. However, laser capsulotomy may sometimes lead to new complications, such as retinal detachment or intraocular pressure rise.

SUMMARY OF THE INVENTION

The present invention seeks to provide an intraocular ring that may be used for mounting therein an intraocular lens (IOL) implant. The ring may be formed with apertures for haptics of the IOL to protrude therethrough. The ring may be easily dialed to a desired position in the capsular bag or other portion of the eye. The ring may be useful in reducing or preventing PCO.

BRIEF DESCRIPTION OF THE DRAWINGS

The present invention will be understood and appreciated more fully from the following detailed description taken in conjunction with the appended drawings in which.

DETAILED DESCRIPTION OF A PREFERRED EMBODIMENT

Figure 1:
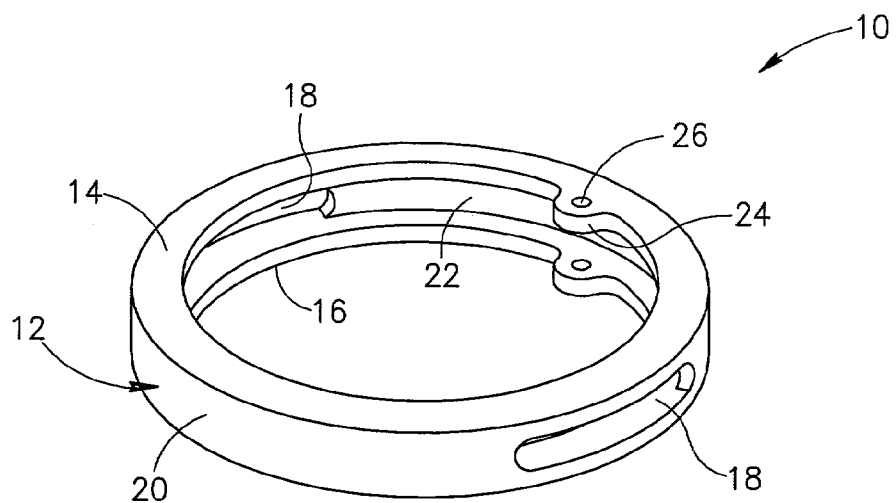
FIGS. 1 and 2 are simplified perspective and plan view illustrations, respectively, of an intraocular ring constructed and operative in accordance with an embodiment of the present invention.
Figure 2:
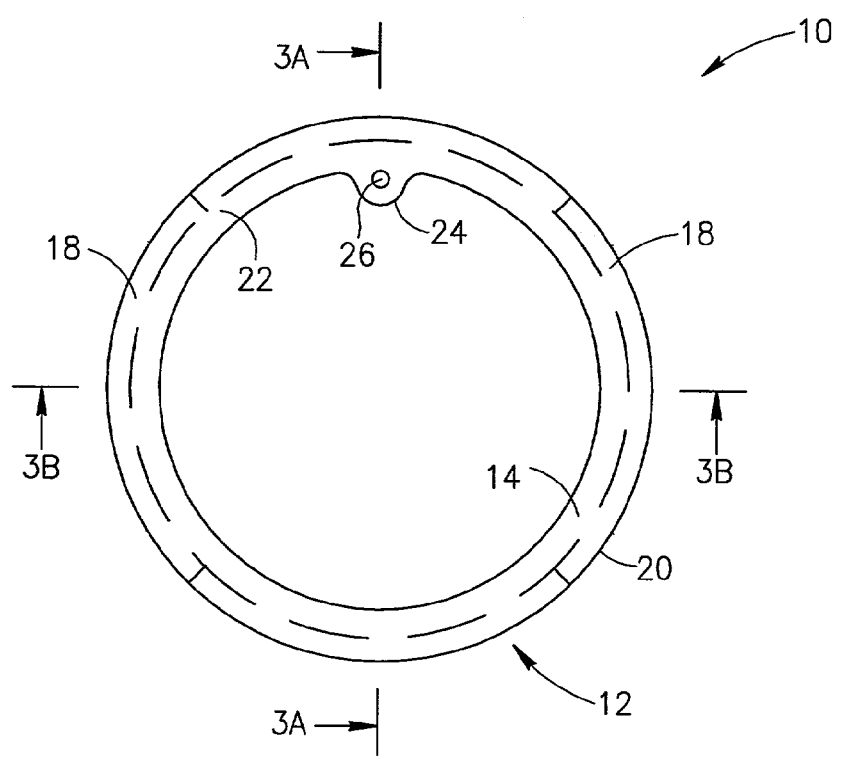
Figure 3A:
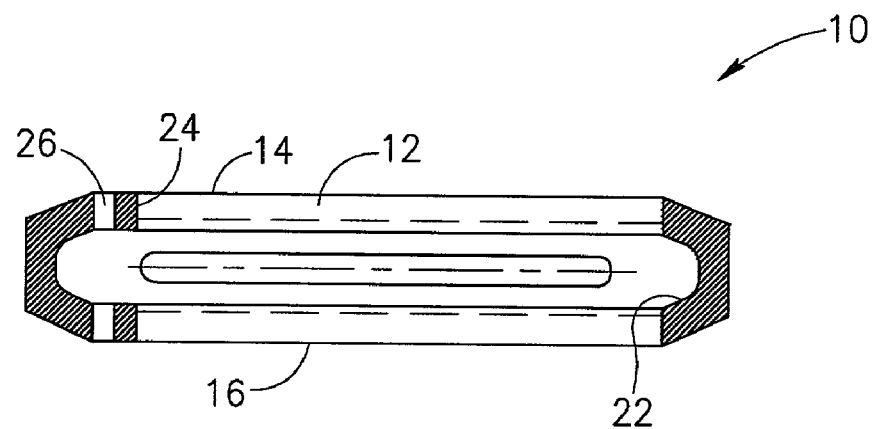
FIGS. 3A and 3B are simplified sectional illustrations of the intraocular ring of FIGS. 1 and 2, taken along lines 3A—3A and 3B—3B respectively in FIG. 2.
Figure 3B:
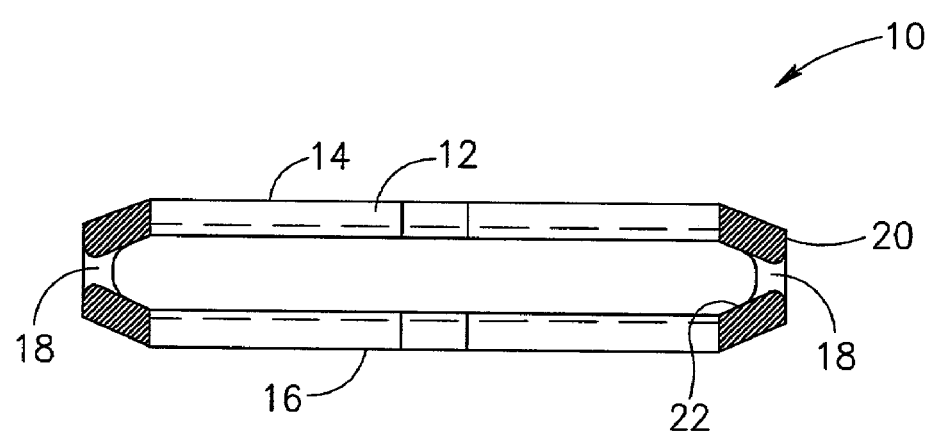
Figure 4:
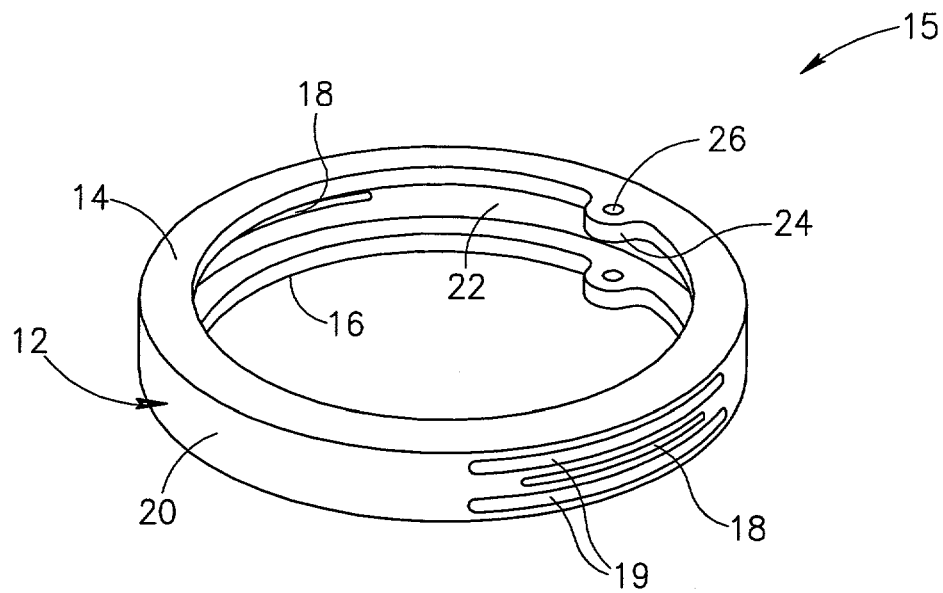
FIGS. 4 and 5 are simplified perspective and plan view illustrations, respectively, of an intraocular ring constructed and operative in accordance with another embodiment of the present invention.
Figure 5:
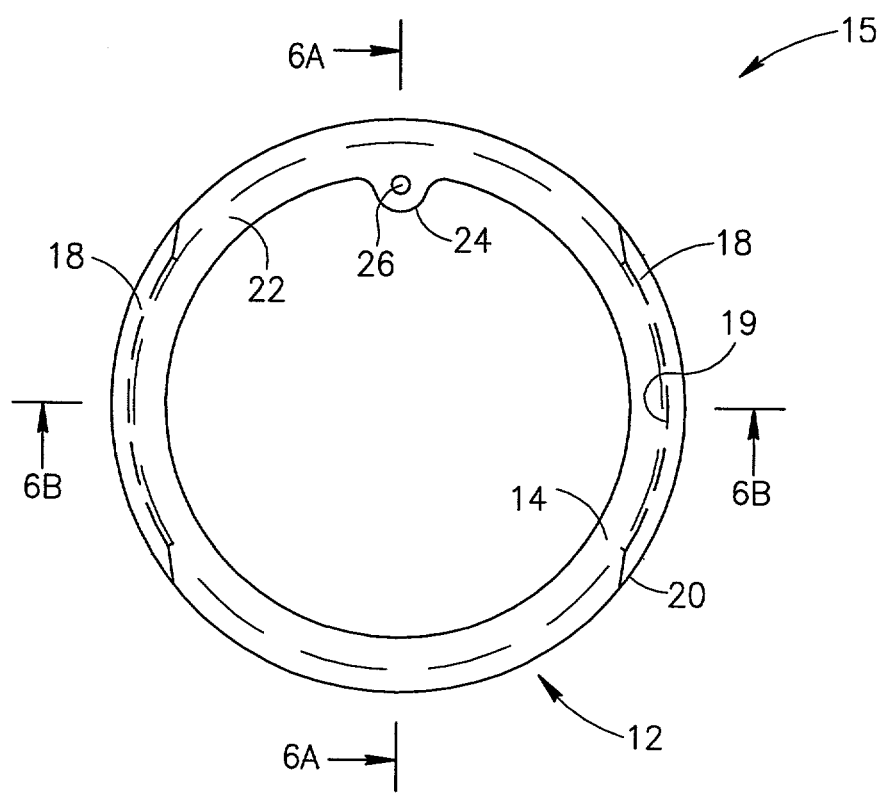
Figure 6A:
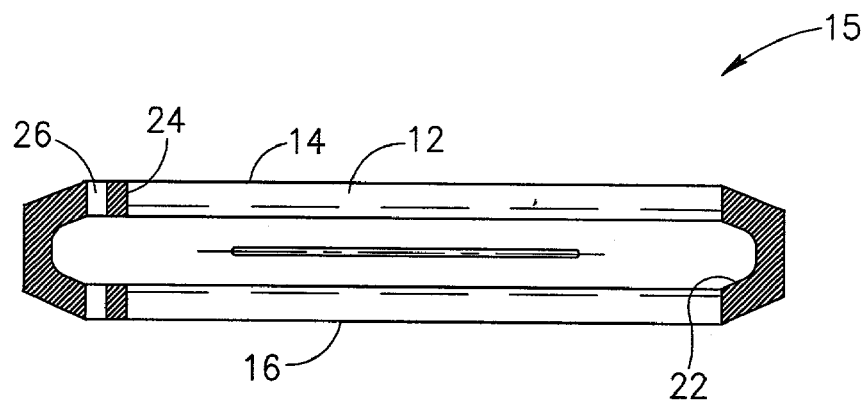
FIGS. 6A and 6B are simplified sectional illustrations of the intraocular ring of FIGS. 4 and 5, taken along lines 6A—6A and 6B—6B respectively in FIG. 5.
Figure 6B:
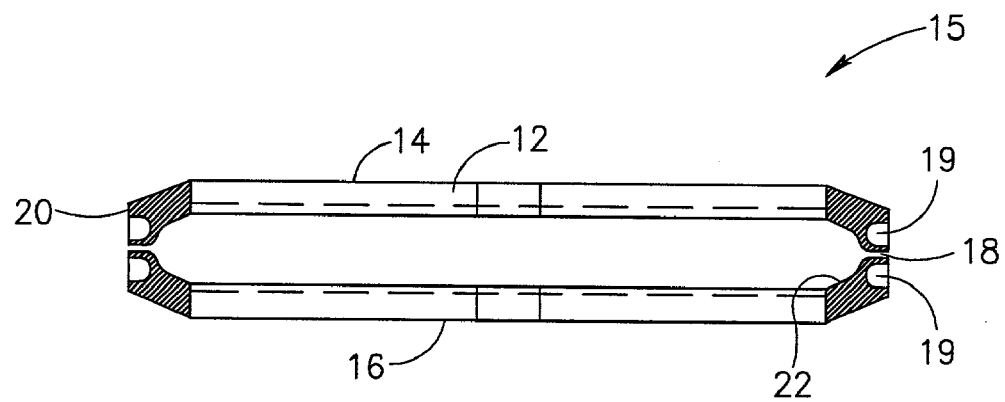

Reference is now made to FIGS. 1, 2, 3A and 3B, which illustrate an intraocular ring 10 constructed and operative in accordance with an embodiment of the present invention.

Ring 10 may comprise a circumferential wall 12, which may serve as the thickness of the ring 10 between an anterior face 14 and a posterior face 16. Wall 12 may be formed with one or more apertures 18, adapted for a haptic of an IOL implant to pass therethrough, as is described hereinbelow with reference to FIG. 3. The one or more apertures 18 may be formed on a surface 20 of wall 12 that faces radially outwards from ring 10.

Ring 10 may be constructed of a biologically compatible material, such as but not limited to, polymethylmethacrylate (PMMA), silicone, silicone rubber, collagen, hydrogel, hyaluronic acid (including the sodium, potassium and other salts thereof), polysulfones, thermolabile materials and other relatively hard or relatively soft and flexible biologically inert materials.

An inner groove 22 may be formed in an inner portion of wall 12 for receiving therein an IOL implant (not shown in FIGS. 1–3B, but shown in FIG. 7).

A dialing member 24 may extend from a portion of ring 12. For example, in the illustrated embodiment, the dialing member 24 may comprise a tab that extends radially inwardly from wall 12, the tab being formed with a hole 26. A tool (not shown) may be inserted in hole 26 for grasping and turning ring 10 about a central axis thereof, so as to dial ring 12 to a desired position in an eye of a patient.

In the embodiment of FIGS. 1–3B, there are two such tabs with holes 26. However, the invention is not limited to this number.

In the embodiment of FIGS. 1–3B, wall 12 is formed with a pair of apertures 18 spaced symmetrically about a center of ring 10. Reference is now made to FIGS. 4–6B, which illustrate an intraocular ring 15 constructed and operative in accordance with another embodiment of the present invention. In this embodiment, wall 12 may comprise one or more sealing members 19 adjacent apertures 18. For example, wall 12 may be formed with one or more circumferential grooves spaced on opposite sides of aperture 18. The grooves may be symmetrically spaced on opposite sides of aperture 18. The sealing members 19 may help form a good seal against haptics of an IOL implant installed in intraocular ring 15, which may be important to reduce or prevent PCO. Ring 10 may also be formed with sealing members 19. It is appreciated that these are just examples of many other possibilities of forming apertures 18 and sealing members 19 in ring 10 or 15.

Figure 7A:
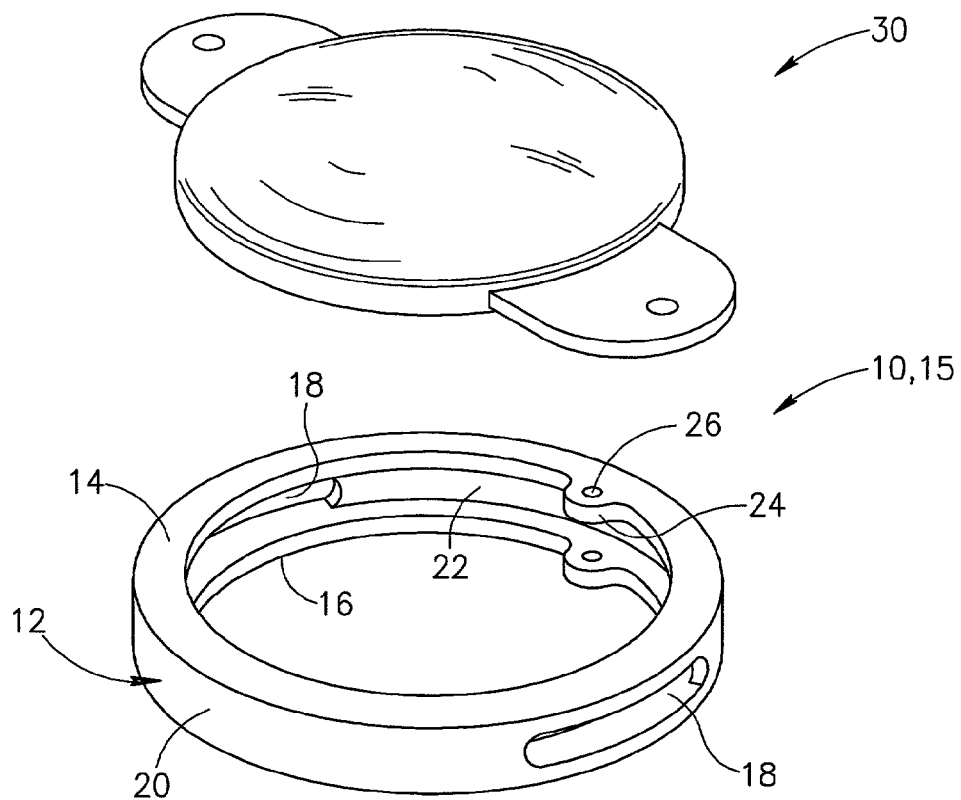
FIGS. 7A and 7B are simplified illustrations of an intraocular lens (IOL) implant, respectively before and after mounting in one of the rings of the invention, showing haptics passing through apertures formed in the ring.
Figure 7B:
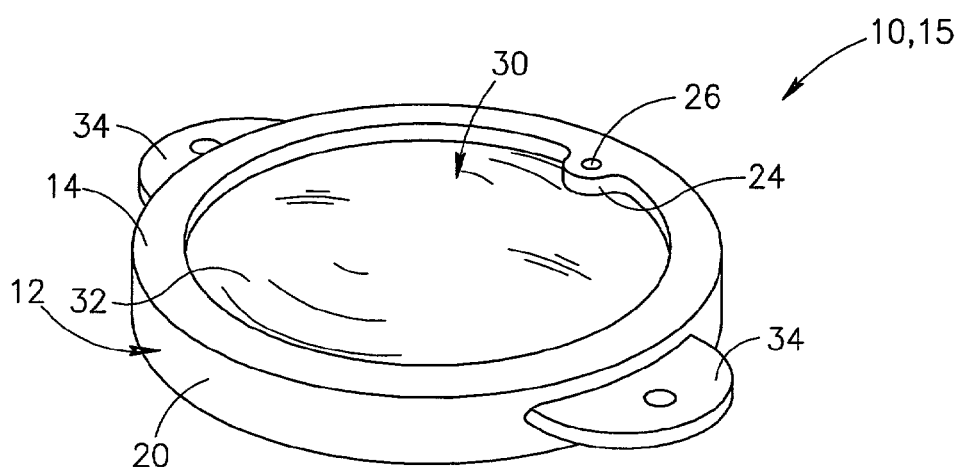

Reference is now made to FIGS. 7A and 7B, which illustrate an IOL implant 30 mounted in ring 10 or 15. IOL implant 30 may include a lens 32 and one or more haptics 34. In the illustrated embodiment, the haptics are plate haptics, but the invention is not limited to this type of haptic, and other sizes and shapes of haptics may be used as well. Haptics 34 may pass through apertures 18. The aperture 18 may be sized such that the haptic 34 is squeezed or press fit therethrough (the terms "squeeze", "press fit" or "tight fit" and the like, being used interchangeably). The tight fit may help prevent migration or formation of lens epithelium cells growing between the lens capsule and IOL implant 30 or ring 10, and thus may reduce or prevent PCO. As noted above, sealing members 19 may also help reduce or prevent PCO.

It will be appreciated by person skilled in the art, that the present invention is not limited by what has been particularly shown and described herein above. Rather the scope of the present invention is defined only by the claims that follow:

What is claimed is:
1. Apparatus comprising:
   an intraocular ring comprising a circumferential wall extending between an anterior face and a posterior face of said ring, said ring being adapted to receive therein an intraocular lens (IOL) implant, and said wall being formed with at least one aperture for passing therethrough a haptic of the IOL implant, said aperture not extending beyond said anterior and posterior faces of said ring, wherein said wall is formed with at least one sealing member adjacent said at least one aperture, wherein said at least one sealing member comprises a plurality of circumferential grooves formed in said wall above and below said aperture such that the grooves are between said anterior face and said aperture and between said aperture and said posterior face.

2. Apparatus according to claim 1, and further comprising a dialing member extending from a portion of said ring, adapted for grasping and turning said ring about a central axis thereof.

3. Apparatus according to claim 2, wherein said dialing member comprises a tab that extends radially inwardly from said wall.

4. Apparatus according to claim 3, wherein said tab is formed with a hole.

5. Apparatus according to claim 1, and further comprising an IOL implant received in said ring, said IOL implant comprising at least one haptic which passes through said at least one aperture.

6. Apparatus according to claim 5, wherein said at least one aperture is sized such that said at least one haptic is press fit therethrough.

7. Apparatus according to claim 1, wherein said wall comprises a surface that faces radially outwards from said ring and said at least one aperture is formed in said surface that faces radially outwards.

8. Apparatus according to claim 1, wherein said ring is formed with an inner groove adapted to receive therein an IOL implant.

9. Apparatus according to claim 8, wherein said inner groove is formed in an inner portion of said wall.

10. Apparatus according to claim 1, wherein said wall is formed with a pair of apertures spaced symmetrically about a center of said ring.

* * * * *